United States Patent
Soong et al.

(10) Patent No.: US 8,273,546 B2
(45) Date of Patent: Sep. 25, 2012

(54) PROCESSES OF PRODUCING FERMENTATION PRODUCTS

(75) Inventors: Chee-Leong Soong, Raleigh, NC (US); Jiyin Liu, Raleigh, NC (US); Guillermo Coward-Kelly, Wake-Forrest, NC (US)

(73) Assignee: Novozymes North America, Inc., Franklinton, NC (US)

( * ) Notice: Subject to any disclaimer, the term of this patent is extended or adjusted under 35 U.S.C. 154(b) by 269 days.

(21) Appl. No.: 12/682,411

(22) PCT Filed: Oct. 20, 2008

(86) PCT No.: PCT/US2008/080507
§ 371 (c)(1),
(2), (4) Date: Apr. 27, 2010

(87) PCT Pub. No.: WO2009/052500
PCT Pub. Date: Apr. 23, 2009

(65) Prior Publication Data
US 2010/0216201 A1    Aug. 26, 2010

Related U.S. Application Data

(60) Provisional application No. 60/980,885, filed on Oct. 18, 2007.

(51) Int. Cl.
*C12P 1/00* (2006.01)
*C12P 7/06* (2006.01)
*C12N 9/00* (2006.01)
*C12N 1/20* (2006.01)
*C12N 15/00* (2006.01)
*C07H 21/04* (2006.01)

(52) U.S. Cl. ........ 435/41; 435/161; 435/183; 435/252.3; 435/320.1; 536/23.2

(58) Field of Classification Search .................. None
See application file for complete search history.

(56) References Cited

FOREIGN PATENT DOCUMENTS

| WO | WO 98/36084 | 8/1998 |
|---|---|---|
| WO | WO 01/60752 | 8/2001 |
| WO | WO 01/62947 | 8/2001 |
| WO | WO 2008/076738 | 6/2008 |

OTHER PUBLICATIONS

Xie et al. Curr Opin Chem Biol. Dec. 2005;9(6):548-54. Epub Nov. 2, 2005.*
Polycarpo et al. Proc Natl Acad Sci U S A. Aug. 24, 2004;101(34):12450-4. Epub Aug. 16, 2004.*
Tripp et al., Carbonic anhydrase: new insights for an ancient enzyme, Journal of Biological Chemistry, American Society of Biochemical Biologists, vol. 276, No. 52, pp. 48615-48618 (2001).
Aguilera et al., Carbonic anhydrase (Nce103p): an essential biosynthetic enzyme for growth of *Saccharomyces cerevisiae* at atmospheric carbon dioxide pressure Biochemical Journal, vol. 391, No. Part 2, pp. 311-316 (2005).
International Search Report issued in corresponding international application No. PCT/US2008/080507 dated Mar. 26, 2009.

* cited by examiner

*Primary Examiner* — Christian Fronda
(74) *Attorney, Agent, or Firm* — Elias Lambiris

(57) ABSTRACT

The invention relates to a process of fermenting plant material in a fermentation medium into a fermentation product using a fermenting organism, wherein one or more carbonic anhydrases are present in the fermentation medium.

10 Claims, 1 Drawing Sheet

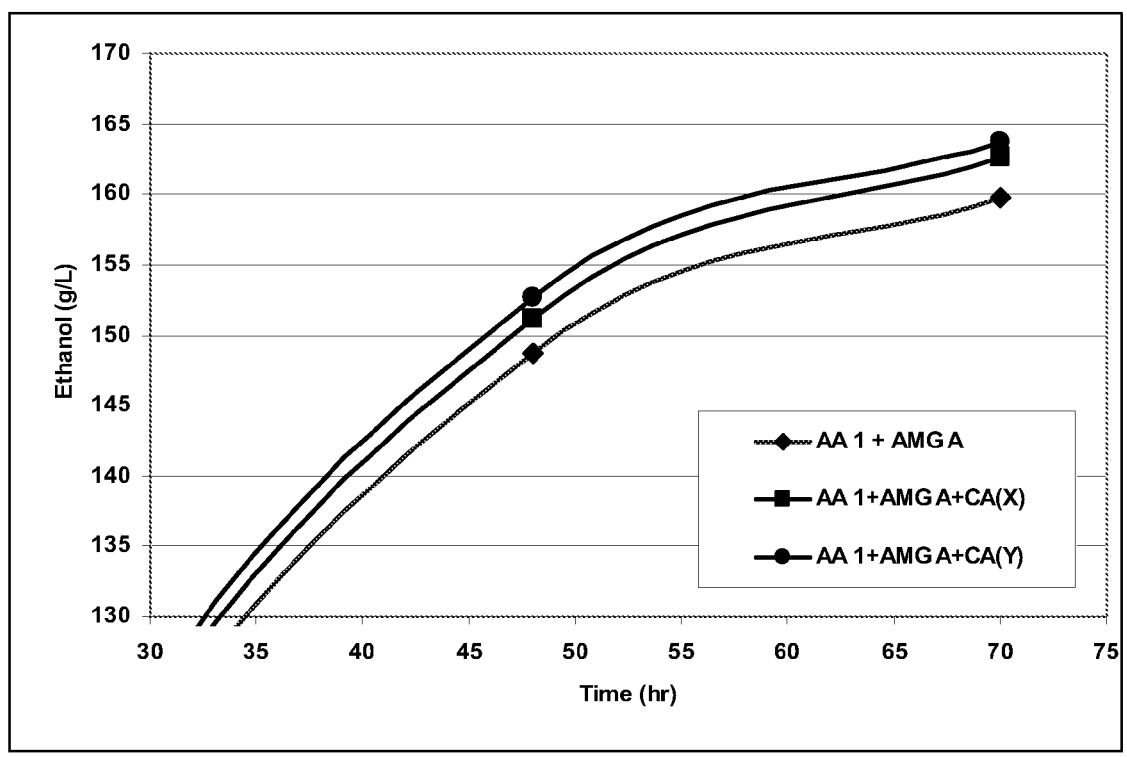

PROCESSES OF PRODUCING FERMENTATION PRODUCTS

CROSS-REFERENCE TO RELATED APPLICATIONS

This application is a 35 U.S.C. 371 national application of PCT/US2008/080507 filed Oct. 20, 2008, which claims priority or the benefit under 35 U.S.C. 119 of U.S. provisional application no. 60/980,885 filed Oct. 18, 2007, the contents of which are fully incorporated herein by reference.

TECHNICAL FIELD

The present invention relates to processes of fermenting plant material into desired fermentation products. The invention also relates to processes of producing a fermentation product from plant material using one or more fermenting organisms and to compositions that can be used in such processes.

BACKGROUND ART

Due to the limited reserves of fossil fuels and worries about emission of greenhouse gasses there is an increasing focus on using renewable energy sources such as plant material.

A vast number of processes of producing fermentation products, especially biofuel products such as ethanol and butanol, by fermentation of sugars derived from starch-containing and/or lignocellulose-containing material are known in the art.

However, production of such fermentation products from plant materials is still too costly. Therefore, there is a need for providing processes that can reduce production costs.

SUMMARY OF THE INVENTION

In the first aspect the invention relates to processes of fermenting plant material in a fermentation medium into a fermentation product using a fermenting organism, wherein one or more carbonic anhydrases are present in the fermentation medium.

In the second aspect the invention relates to processes of producing a fermentation product from starch-containing material comprising the steps of:
i) liquefying starch-containing material with an alpha-amylase;
ii) saccharifying the liquefied material with a carbohydrate source generating enzyme,
iii) fermenting with one or more fermenting organisms in accordance with a fermentation process of the invention.

In the third aspect the invention relates to processes of producing a fermentation product from starch-containing material, comprising the steps of:
(a) saccharifying starch-containing material at a temperature below the initial gelatinization temperature of said starch-containing material,
(b) fermenting using a fermenting organism,
wherein fermentation is carried out in accordance with a fermentation process of the invention.

In the fourth aspect the invention relates to processes of producing a fermentation product from lignocellulose-containing material, comprising the steps of:
(a) pre-treating lignocellulose-containing material:
(b) hydrolysing the material;
(c) fermenting using a fermenting organism in accordance with a fermentation process of the invention.

In the fifth aspect the invention relates to a composition comprising one or more carbonic anhydrases and one or more alpha-amylases.

In the sixth aspect the invention relates to the use of a carbonic anhydrase for controlling pH fluctuation during fermentation.

In the seventh aspect the invention relates to the use of carbonic anhydrase for improving the yeast fermentation product yield and/or fermentation rate.

In the final aspect the invention relates to a transgenic plant material transformed with one or more carbonic anhydrase genes.

BRIEF DESCRIPTION OF THE FIGURES

FIG. 1 shows the effect of carbonic anhydrase of (CA) toward alpha-amylase (AA 1) and glucoamylase (AMG A) combo in one-step fermentation process.

DETAILED DESCRIPTION OF THE INVENTION

The present invention relates to processes of fermenting plant material into a desired fermentation product. The invention also provides processes of producing desired fermentation products from plant material using a fermenting organism. Finally the invention relates to a composition comprising one or more enzymes and one or more fermentation product boosting compounds.

The inventors have observed that the pH at some point in time during yeast fermentation of plant material decreases to a pH below 4.5. The low pH is a drawback as some enzymes, especially alpha-amylases, undergo denaturation and/or autocleavage. The inventors have found a solution to this problem. The concept of this invention is using carbonic anhydrase to convert $CO_2$, a by-product of yeast fermentation, to bicarbonate. The chemical equation $C_6H_{12}O_6 \rightarrow 2C_2H_5OH + 2CO_2$ summarizes ethanol fermentation, in which one hexose molecule is converted into two ethanol molecules and two carbon dioxide molecules. Carbonic anhydrase can reversibly catalyze the reaction of the by-product $CO_2$ and water to bicarbonate and a proton ($CO_2 + H_2O \rightarrow HCO_3^- H^+$); a reaction that is slow at physiological pH and requires enzyme catalysis.

Without being bound by any particular theory, the addition of carbonic anhydrase to a fermentation process is believed to serve at least two functions:
(1) The carbon dioxide by-product is removed from the sugar fermentation reaction equilibrium due to carbonic anhydrase catalysis and thereby balancing the reaction equilibrium towards the desired ethanol product.
(2) Reduce or prevent re-conversion of bicarbonate to $CO_2$, the bicarbonate may react with the existing cations (potassium, calcium or magnesium) present in the fermentation medium to bicarbonate salt and effectively serve as buffering agent to stabilize pH fluctuation during fermentation.

Utilizing carbonic anhydrase as a mean to maintain pH (preferably above pH 4.5) facilitates using enzymes for producing fermentation products, such as biofuels, from starch and/or lignocellulose (i.e. biomass) with enzymes that may be less stable at low pH but are highly active on starch or other substrates such as cellulose or hemicellulose. Moreover, maintaining pH above 4.5 will also favor fermenting organisms, such as especially yeast which has an optimum fermentation performance at about pH 5.0.

In addition, bicarbonate was reported to be involved in inorganic carboxylations of some metabolic reactions in yeast (Biochem J. 391, 311-316); in particular when urea is added as nitrogen source. Urea is metabolized by bicarbonate-dependent urea carboxylase (J. Biol. Chem., 247, 1349-1353). Thus, applying carbonic anhydrase may appropriately provide the bicarbonate needed for yeast's urea metabolism.

Consequently, in the first aspect the invention relates to processes of fermenting plant material in a fermentation medium into a fermentation product using a fermenting organism, wherein one or more carbonic anhydrases are present in the fermentation medium. The carbonic anhydrase may be added/introduced before and/or during fermentation and/or may be produced in situ by overexpression by the fermenting organisms, preferably yeast.

According to the invention the starting material (i.e., substrate for the fermenting organism) may be any plant material or part or constituent thereof.

In one embodiment the stating material is starch-containing material. In another embodiment the starch material is lignocellulose-containing material.

Fermenting Organisms

The term "fermenting organism" refers to any organism, including bacterial and fungal organisms, including yeast and filamentous fungi, suitable for producing a desired fermentation product. The fermenting organism may be C6 or C5 fermenting organisms, or a combination thereof. Both C6 and C5 fermenting organisms are well known in the art.

Especially suitable fermenting organisms according to the invention are able to ferment, i.e., convert, sugars such as glucose, fructose, maltose, xylose, mannose and/or arabinose, directly or indirectly into the desired fermentation product.

Examples of fermenting organisms include fungal organisms such as yeast. Preferred yeast includes strains of the genus *Saccharomyces*, in particular strains of *Saccharomyces cerevisiae* or *Saccharomyces uvarum*; a strain of *Pichia*, preferably *Pichia stipitis* such as *Pichia stipitis* CBS 5773 or *Pichia pastoris*; a strain of the genus *Candida*, in particular a strain of *Candida utills, Candida arabinofermentans, Candida diddensii, Candida sonorensis, Candida shehatae, Candida tropicalis*, or *Candida boidinli*. Other fermenting organisms include strains of *Hansenula*, in particular *Hansenula polymorpha* or *Hansenula anomala; Kluyveromyces*, in particular *Kluyveromyces fragilis* or *Kluyveromyces marxianus*; and *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of *Zymobacter*, in particular *Zymobactor palmae*, strains of *Klebsiella* in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes* and strains of *Thermoanaerobacter*, in particular *Thermoanaembacter BG1L1* (*Appl. Microbiol. Biotech*, 77: 61-86) and *Thermoanarobacter ethanolicus, Thermoanaerobacter thermosaccharolyticum*, or *Thermoanaerobacter mathranii*. Strains of *Lactobacillus* are also envisioned as are strains of *Corynebacterium glutamicum* R, *Bacillus thermoglucosidaisus*, and *Geobacillus thermoglucosidasius*.

In an embodiment the fermenting organism is a C6 sugar fermenting organism, such as a strain of, e.g., *Saccharomyces cerevisiae*.

In connection with fermentation of lignocellulose derived materials, C5 sugar fermenting organisms are contemplated. Most C5 sugar fermenting organisms also ferment C6 sugars. Examples of C5 sugar fermenting organisms include strains of *Pichia*, such as of the species *Pichia stipitis*. C5 sugar fermenting bacteria are also known. Also some *Saccharomyces cerevisae* strains ferment C5 (and C6) sugars. Examples are genetically modified strains of *Saccharomyces* spp. that are capable of fermenting C5 sugars include the ones concerned in, e.g., Ho et al., 1998, *Applied and Environmental Microbiology*, p. 1852-1859 and Karhumaa et al., 2006, *Microbial Cell Factories* 5:18, and Kuyper et al., 2005, *FEMS Yeast Research* 5, p. 925-934.

Certain fermenting organisms' fermentative performance may be inhibited by the presence of inhibitors in the fermentation media and thus reduce ethanol production capacity. Compounds in biomass hydrosylates and high concentrations of ethanol are known to inhibit the fermentative capacity of certain yeast cells. Pre-adaptation or adaptation methods may reduce this inhibitory effect. Typically pre-adaptation or adaptation of yeast cells involves sequentially growing yeast cells, prior to fermentation, to increase the fermentative performance of the yeast and increase ethanol production. Methods of yeast pre-adaptation and adaptation are known in the art. Such methods may include, for example, growing the yeast cells in the presence of crude biomass hydrolyzates; growing yeast cells in the presence of inhibitors such as phenolic compounds, furaldehydes and organic acids; growing yeast cells in the presence of non-inhibiting amounts of ethanol; and supplementing the yeast cultures with acetaldehyde. In one embodiment, the fermenting organism is a yeast strain subject to one or more pre-adaptation or adaptation methods prior to fermentation.

Certain fermenting organisms such as yeast require an adequate source of nitrogen for propagation and fermentation. Many sources of nitrogen can be used and such sources of nitrogen are well known in the art, in one embodiment, a low cost source of nitrogen is used. Such low cost sources can be organic, such as urea, DDGs, wet cake or corn mash, or inorganic, such as ammonia or ammonium hydroxide.

Commercially available yeast suitable for ethanol production includes, e.g., ETHANOL RED™ yeast (available from Fermentis/Lesaffre, USA), FALI™ (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

According to the invention the fermenting organism capable of producing a desired fermentation product from fermentable sugars, such as e.g., glucose, fructose and/or maltose, is preferably grown under precise conditions at a particular growth rate. When the fermenting organism is introduced into/added to the fermentation medium the inoculated fermenting organism pass through a number of stages. Initially growth does not occur. This period is referred to as the "lag phase" and may be considered a period of adaptation. During the next phase referred to as the "exponential phase" the growth rate gradually increases. After a period of maximum growth the rate ceases and the fermenting organism enters "stationary phase". After a further period of time the fermenting organism enters the "death phase" where the number of viable cells declines.

In one embodiment the carbonic anhydrase(s) is(are) added to the fermentation medium when the fermenting organism is in lag phase.

In one embodiment the carbonic anhydrase(s) is(are) added to the fermentation medium when the fermenting organism is in exponential phase.

In one embodiment the carbonic anhydrase is(are) added to the fermentation medium when the fermenting organism is in stationary phase.

Fermentation Products

The term "fermentation product" means a product produced by a process that includes a fermentation step using a fermenting organism. Fermentation products contemplated according to the invention include any fermentation product, especially biofuels products such as ethanol and butanol.

Fermentation

The fermentation may according to the invention be carried out at conventionally used conditions. Preferred fermentation processes are anaerobic processes.

For ethanol production the fermentation may in one embodiment go on for 6 to 120 hours, in particular 24 to 96 hours. In an embodiment the fermentation is carried out at a temperature between 25 to 40° C., preferably 28 to 35° C., such as 30° C. to 34° C., and in particular around 32° C. In an embodiment the pH when initiating fermentation is in the range from pH 3 to 6, preferably around pH 4 to 5.

Contemplated is a simultaneous hydrolysis/saccharification and fermentation (SHF/SSF) where there is no separate holding stage for the hydrolysis/saccharification, meaning that the hydrolyzing/saccharifying enzyme(s), the fermenting organism and carbonic anhydrase(s) may be added together. However, it should be understood that the carbonic anhydrase(s) may also be added separately. When fermentation is performed simultaneous with hydrolysis/saccharification the temperature is preferably between 25 to 40° C., preferably 28 to 35° C., such as 30° C. to 34° C., in particular around 32° C., when the fermentation organism is a strain of *Saccharomyces cerevisiae* and the desired fermentation product is ethanol.

Other fermentation products may be fermented at temperatures known to the skilled person in the art to be suitable for the fermenting organism in question.

The process of the invention may be performed as a batch or as a continuous process. The fermentation process of the invention may be conducted in an ultrafiltration system where the retentate is held under recirculation in the presence of solids, water, and the fermenting organism, and where the permeate is the desired fermentation product containing liquid. Equally contemplated if the process is conducted in a continuous membrane reactor with ultrafiltration membranes and where the retentate is held under recirculation in presence of solids, water, the fermenting organism and where the permeate is the fermentation product containing liquid.

After fermentation the fermenting organism may be separated from the fermented slurry and recycled to the fermentation medium.

Recovery

Subsequent to fermentation the fermentation product may be separated from the fermentation medium. The slurry may be distilled to extract the desired fermentation product or the desired fermentation product may be extracted from the fermentation medium by micro or membrane filtration techniques. Alternatively the fermentation product may be recovered by stripping. Methods for recovery are well known in the art.

Production of Fermentation Products from Starch-Containing Material

Processes for Producing Fermentation Products from Gelatinized Starch-Containing Material In this aspect the present invention relates to a process for producing a fermentation product, especially ethanol, from starch-containing material, which process includes a liquefaction step and sequentially or simultaneously performed saccharification and fermentation steps.

The invention relates to a process for producing a fermentation product from starch-containing material comprising the steps of:

i) liquefying starch-containing material with an alpha-amylase;

ii) saccharifying the liquefied material with a carbohydrate source generating enzyme, iii) fermenting using one or more fermenting organisms, wherein fermentation is carried out in accordance with the invention, i.e., in the presence of carbonic anhydrase.

Saccharification step ii) and fermentation step iii) may be carried out either sequentially or simultaneously. The carbonic anhydrase may be added before and/or during the fermentation step.

The fermentation product, such as especially ethanol, may optionally be recovered after fermentation, e.g., by distillation. Suitable starch-containing starting materials are listed in the section "Starch-containing materials" section below. Contemplated enzymes are listed in the "Enzymes" section below. The liquefaction is preferably carried out in the presence of an alpha-amylase, preferably a bacterial alpha-amylase or acid fungal alpha-amylase. The fermenting organism is preferably yeast, preferably a strain of *Saccharomyces*. Suitable fermenting organisms are listed in the "Fermenting Organisms" section above.

In a particular embodiment, the process of the invention further comprises, prior to the step (i), the steps of:

x) reducing the particle size of the starch-containing material, preferably by milling;

y) forming a slurry comprising the starch-containing material and water.

The aqueous slurry may contain from 10-55 wt.-% dry solids, preferably 25-45 wt.-% dry solids (DS), more preferably 30-40% dry solids of starch-containing material. The slurry is heated to above the gelatinization temperature and alpha-amylase, preferably bacterial and/or acid fungal alpha-amylase may be added to initiate liquefaction (thinning). The slurry may in an embodiment be jet-cooked to further gelatinize the slurry before being subjected to an alpha-amylase in step (i) of the invention.

More specifically liquefaction may be carried out as a three-step hot slurry process. The slurry is heated to between 60-95° C., preferably 80-85° C., and alpha-amylase is added to initiate liquefaction (thinning). Then the slurry may be jet-cooked at a temperature between 95-140° C., preferably 105-125° C., for 1-15 minutes, preferably for 3-10 minutes, especially around 5 minutes. The slurry is cooled to 60-95° C. and more alpha-amylase is added to finalize hydrolysis (secondary liquefaction). The liquefaction process is usually carried out at pH 4.5-6.5, in particular at a pH between 5 and 6. Milled and liquefied whole grains are known as mash.

The saccharification in step (ii) may be carried out using conditions well know in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5.

The most widely used process in fermentation product, especially ethanol, production is the simultaneous saccharification and fermentation (SSF) process, in which there is no holding stage for the saccharification, meaning that fermenting organism, such as yeast, and enzyme(s) may be added together. SSF may typically be carried out at a temperature between 25° C. and 40° C., such as between 28° C. and 35° C., such as between 30° C. and 34° C., preferably around 32° C. According to the invention the temperature may be adjusted up or down during fermentation.

In accordance with the present invention the fermentation step (iii) includes, without limitation, fermentation processes of the invention used to produce fermentation products as exemplified above in the "Fermentation Products" section.

Processes for Producing Fermentation Products from Un-Gelatinized Starch-Containing In this aspect the invention relates to processes for producing a fermentation product from starch-containing material without gelatinization (often referred to as "cooking") of the starch-containing material. According to the invention the desired fermentation product, such as ethanol, can be produced without liquefying the aqueous slurry containing the starch containing material. In one embodiment a process of the invention includes saccharifying (e.g., milled) starch-containing material, e.g., granular starch, below the initial gelatinization temperature, preferably in the presence of an alpha-amylase and/or an carbohydrate-source generating enzyme to produce sugars that can be fermented into the desired fermentation product by a suitable fermenting organism.

In this embodiment the desired fermentation product, preferably ethanol, is produced from ungelatinized (i.e., uncooked), preferably milled corn.

Accordingly, in this aspect the invention relates to a process of producing a fermentation product from starch-containing material, comprising the steps of:

(a) saccharifying starch-containing material at a temperature below the initial gelatinization temperature of said starch-containing material, (b) fermenting using a fermenting organism, wherein the fermentation is carried out in accordance with the fermentation process of the invention, i.e., in the presence of carbonic anhydrase.

In a preferred embodiment steps (a) and (b) are carried out simultaneously (i.e., one step fermentation) or sequentially.

The fermentation product, such as especially ethanol, may optionally be recovered after fermentation, e.g., by distillation. Suitable starch-containing starting materials are listed in the section "Starch-Containing materials" section below. Contemplated enzymes are listed in the "Enzymes" section below. The alpha-amylase used is preferably an acid alpha-amylase, preferably acid fungal alpha-amylase. The fermenting organism is preferably yeast, preferably a strain of *Saccharomyces*. Suitable fermenting organisms are listed in the "Fermenting Organisms"-section above.

The term "initial gelatinization temperature" means the lowest temperature at which gelatinization of the starch commences. In general starch heated in water begins to gelatinize between 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In context of this invention the initial gelatinization temperature of a given starch-containing material may be determined as the temperature at which birefringence is lost in 5% of the starch granules using the method described by Gorinstein, S. and Lii, C., Starch/Stärke, Vol. 44 (12) pp. 461-466 (1992).

Before step (a) a slurry of starch-containing material, such as granular starch, having 10-55 wt.-% dry solids (DS), preferably 25-45 wt.-% dry solids, more preferably 30-40% dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the gelatinization temperature and thus no significant viscosity increase takes place, high levels of stillage may be used if desired. In an embodiment the aqueous slurry contains from about 1 to about 70 vol.-% stillage, preferably 15-60% vol.-% stillage, especially from about 30 to 50 vol.-% stillage.

The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material is converted into a soluble starch hydrolysate.

A process of the invention is conducted at a temperature below the initial gelatinization temperature, which means that the temperature at which step (a) is carried out typically lies in the range between 30-75° C., preferably between 45-60° C.

In a preferred embodiment step (a) and step (b) are carried out as a simultaneous saccharification and fermentation process. In such preferred embodiment the process is typically carried at a temperature between 25° C. and 40° C., such as between 28° C. and 35° C., such as between 30° C. and 34° C., preferably around 32° C.

In an embodiment simultaneous saccharification and fermentation is carried out so that the sugar level, such as glucose level, is kept at a low level such as below 6 wt.-%, preferably below about 3 wt.-%, preferably below about 2 wt.-%, more preferred below about 1 wt.-%., even more preferred below about 0.5%, or even more preferred 0.25% wt.-%, such as below about 0.1 wt.-%. Such low levels of sugar can be accomplished by simply employing adjusted quantities of enzyme and fermenting organism. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt.-% or below about 0.2 wt.-%.

The process of the invention may be carried out at a pH in the range between 3 and 7, preferably from pH 3.5 to 6, or more preferably from pH 4 to 5.

Starch-Containing Materials

Any suitable starch-containing starting material, including granular starch, may be used according to the present invention. The starting material is generally selected based on the desired fermentation product. Examples of starch-containing starting materials suitable for use in a process of present invention include tubers, roots, stems, whole grains, corns, cobs, wheat, barley, rye, milo, sago, cassava, tapioca, sorghum, rice peas, beans, or sweet potatoes, or mixtures thereof, or cereals. Contemplated are also waxy and non-waxy types of corn and barley.

The term "granular starch" means uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch-containing materials comprising milled whole grain including non-starch fractions such as germ residues and fibers. The raw material, such as whole grain, is reduced in particle size, e.g., by milling, in order to open up the structure and allowing for further processing. Two processes are preferred according to the invention: wet and dry milling. In dry milling whole kernels are milled and used. Wet milling gives a good separation of germ and meal (starch granules and protein) and is often applied at locations where the starch hydrolysate is used in production of syrups. Both dry and wet milling is well known in the art of starch processing and is equally contemplated for the process of the invention. In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen.

Production of Fermentation Products from Lignocellulose-Containing Material

In this aspect, the invention relates to processes of producing fermentation products from lignocellulose-containing material. Conversion of lignocellulose-containing material into fermentation products, such as ethanol, has the advantages of the ready availability of large amounts of feedstock, including wood, agricultural residues, herbaceous crops, municipal solid wastes etc. Lignocellulose-containing materials primarily consist of cellulose, hemicellulose, and lignin and are often referred to as "biomass".

The structure of lignocellulose is not directly accessible to enzymatic hydrolysis. Therefore, the lignocellulose-containing material has to be pre-treated, by acid hydrolysis under adequate conditions of pressure and temperature, in order to break the lignin seal and disrupt the crystalline structure of cellulose. This causes solubilization of the hemicellulose and cellulose fractions. The cellulose and hemicelluloses can then be hydrolyzed enzymatically, e.g., by cellulolytic enzymes, to convert the carbohydrate polymers into fermentable sugars which may be fermented into desired fermentation products, such as ethanol. Optionally the fermentation product may be recovered, e.g., by distillation.

In this aspect the invention relates to a process of producing a fermentation product from lignocellulose-containing material, comprising the steps of:
(a) pre-treating lignocellulose-containing material;
(b) hydrolyzing the material;
(c) fermenting with a fermenting organism in accordance with the fermentation process of the invention, i.e., in the presence of carbonic anhydrase.

The carbonic anhydrase may be added before and/or during fermentation. Hydrolysis steps (b) and fermentation step (c) may be carried out sequentially or simultaneously. In preferred embodiments the steps are carried out as SHF or HHF process steps which will be described further below.

SSF, HHF and SHF

Hydrolysis and fermentation can be carried out as a simultaneous hydrolysis and fermentation step (SSF). In general this means that combined/simultaneous hydrolysis and fermentation are carried out at conditions (e.g., temperature and/or pH) suitable, preferably optimal, for the fermenting organism(s) in question.

Hydrolysis and fermentation can also be carried out as hybrid hydrolysis and fermentation (HHF). HHF typically begins with a separate partial hydrolysis step and ends with a simultaneous hydrolysis and fermentation step. The separate partial hydrolysis step is an enzymatic cellulose saccharification step typically carried out at conditions (e.g., at higher temperatures) suitable, preferably optimal, for the hydrolyzing enzyme(s) in question. The subsequent simultaneous hydrolysis and fermentation step is typically carried out at conditions suitable for the fermenting organism(s) (often at lower temperatures than the separate hydrolysis step).

Hydrolysis and fermentation can also be carried out as separate hydrolysis and fermentation, where the hydrolysis is taken to completion before initiation of fermentation. This is often referred to as "SHF".

Pre-Treatment

The lignocellulose-containing material may according to the invention be pre-treated before being hydrolyzed and/or fermented. In a preferred embodiment the pre-treated material is hydrolyzed, preferably enzymatically, before and/or during fermentation. The goal of pre-treatment is to separate and/or release cellulose, hemicellulose and/or lignin and this way improve the rate of enzymatic hydrolysis.

According to the invention pre-treatment step (a) may be a conventional pre-treatment step known in the art. Pre-treatment may take place in aqueous slurry. The lignocellulose-containing material may during pre-treatment be present in an amount between 10-80 wt. %, preferably between 20-50 wt.-%.

Chemical, Mechanical and/or Biological Pre-Treatment

The lignocellulose-containing material may according to the invention be chemical, mechanically and/or biologically pre-treated before hydrolysis and/or fermentation. Mechanical treatment (often referred to as physical pre-treatment) may be used alone or in combination with subsequent or simultaneous hydrolysis, especially enzymatic hydrolysis, to promote the separation and/or release of cellulose, hemicellulose and/or lignin.

Preferably, the chemical, mechanical and/or biological pre-treatment is carried out prior to the hydrolysis and/or fermentation. Alternatively, the chemical, mechanical and/or biological pre-treatment is carried out simultaneously with hydrolysis, such as simultaneously with addition of one or more cellulolytic enzymes, or other enzyme activities mentioned below, to release fermentable sugars, such as glucose and/or maltose.

In an embodiment of the invention the pre-treated lignocellulose-containing material is washed and/or detoxified before hydrolysis step (b). This may improve the fermentability of, e.g., dilute-acid hydrolyzed lignocellulose-containing material, such as corn stover. Detoxification may be carried out in any suitable way, e.g., by steam stripping, evaporation, ion exchange, resin or charcoal treatment of the liquid fraction or by washing the pre-treated material.

Chemical Pre-Treatment

According to the present invention "chemical pre-treatment" refers to any chemical treatment which promotes the separation and/or release of cellulose, hemicellulose and/or lignin. Examples of suitable chemical pre-treatment steps include treatment with: for example, dilute acid, lime, alkaline, organic solvent, ammonia, sulfur dioxide, carbon dioxide. Further, wet oxidation and pH-controlled hydrothermolysis are also contemplated chemical pre-treatments.

Preferably, the chemical pre-treatment is acid treatment, more preferably, a continuous dilute and/or mild acid treatment, such as, treatment with sulfuric acid, or another organic acid, such as acetic acid, citric acid, tartaric acid, succinic acid, or mixtures thereof. Other acids may also be used. Mild acid treatment means in the context of the present invention that the treatment pH lies in the range from 1-5, preferably 1-3. In a specific embodiment the acid concentration is in the range from 0.1 to 2.0 wt % acid, preferably sulphuric acid. The acid may be mixed or contacted with the material to be fermented according to the invention and the mixture may be held at a temperature in the range of 166-220° C., such as 165-195° C., for periods ranging from minutes to seconds, e.g., 1-60 minutes, such as 2-30 minutes or 3-12 minutes. Addition of strong acids, such as sulphuric acid, may be applied to remove hemicellulose. This enhances the digestibility of cellulose.

Cellulose solvent treatment, also contemplated according to the invention; has been shown to convert about 90% of cellulose to glucose. It has also been shown that enzymatic hydrolysis could be greatly enhanced when the lignocellulosic structure is disrupted. Alkaline ozone, organosolv (uses Lewis acids, $FeCl_3$, $(Al)_2SO_4$ in aqueous alcohols), glycerol, dioxane, phenol, or ethylene glycol are among solvents known to disrupt cellulose structure and promote hydrolysis (Mosier et al., 2005, Bioresource Technology 96: 673-686).

Alkaline chemical pre-treatment with base, e.g., NaOH, $Na_2CO_3$ and/or ammonia or the like, is also within the scope of the invention. Pre-treatment methods using ammonia are described in, e.g., WO 2006/110891, WO 2006/110899, WO 2006/110900, WO 2006/110901, which are hereby incorporated by reference.

Wet oxidation techniques involve use of oxidizing agents, such as: sulphite based oxidizing agents or the like. Examples of solvent pre-treatments include treatment with DMSO (Dimethyl Sulfoxide) or the like. Chemical pre-treatment is generally carried out for 1 to 60 minutes, such as from 5 to 30 minutes, but may be carried out for shorter or longer periods of time dependent on the material to be pre-treated.

Other examples of suitable pre-treatment methods are described by Schell et al., 2003, Appl. Biochem and Biotechn. 105-108: 69-85, and Mosier et al., 2005, Bioresource Technology 96: 673-686, and US publication no 2002/0164730, which references are hereby all incorporated by reference.

Mechanical Pre-Treatment

As used in context of the present invention the term "mechanical pre-treatment" refers to any mechanical or physical pretreatment which promotes the separation and/or release of cellulose, hemicellulose and/or lignin from lignocellulose-containing material. For example, mechanical pre-treatment includes various types of milling, irradiation, steaming/steam explosion, and hydrothermolysis.

Mechanical pre-treatment includes comminution (mechanical reduction of the particle size). Comminution includes dry milling, wet milling and vibratory ball milling. Mechanical pre-treatment may involve high pressure and/or high temperature (steam explosion). In an embodiment of the invention high pressure means pressure in the range from 300 to 600 psi, preferably 400 to 500 psi, such as around 450 psi. In an embodiment of the invention high temperature means temperatures in the range from about 100 to 300° C., preferably from about 140 to 235° C. In a preferred embodiment mechanical pre-treatment is a batch-process, steam gun hydrolyzer system which uses high pressure and high temperature as defined above. A Sunds Hydrolyzer (available from Sunds Defibrator AB (Sweden) may be used for this.

Combined Chemical and Mechanical Pretreatment

In an embodiment of the invention both chemical and mechanical pre-treatments are carried out involving, for example, both dilute or mild acid pretreatment and high temperature and pressure treatment. The chemical and mechanical pretreatment may be carried out sequentially or simultaneously, as desired.

Accordingly, in a preferred embodiment, the lignocellulose-containing material is subjected to both chemical and mechanical pretreatment to promote the separation and/or release of cellulose, hemicellulose and/or lignin.

In a preferred embodiment the pre-treatment is carried out as a dilute and/or mild acid steam explosion step. In another preferred embodiment pre-treatment is carried out as an ammonia fiber explosion step (or AFEX pretreatment step).

Biological Pre-Treatment

As used in the present invention the term "biological pretreatment" refers to any biological pretreatment which promotes the separation and/or release of cellulose, hemicellulose, and/or lignin from the lignocellulose-containing material. Biological pre-treatment techniques can involve applying lignin-solubilizing microorganisms (see, for example, Hsu, T.-A., 1996, Pretreatment of biomass, in *Handbook On Bioethanol: Production and Utilization*, Wyman, C. E., ed., Taylor & Francis, Washington, D.C., 179-212; Ghosh, P., and Singh, A., 1993, Physicochemical and biological treatments for enzymatic/microbial conversion of lignocellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566. American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson, L., and Hahn-Hagerdal, B., 1996, Fermentation of lignocellulosic hydrolysates for ethanol production, *Enz. Microb. Tech.* 18: 312-331; and Vallander, L., and Eriksson, K.-E. L., 1990, Production of ethanol from lignocellulosic materials: State of the art, *Adv. Biochem. Eng./Biotechnol.* 42: 63-95).

Hydrolysis

Before and/or during fermentation the pre-treated lignocellulose-containing material may be hydrolyzed in order to break the lignin seal and disrupt the crystalline structure of cellulose. In a preferred embodiment hydrolysis is carried out enzymatically. According to the invention the pre-treated lignocellulose-containing material to be fermented may be hydrolyzed by one or more hydrolases (class EC 3 according to Enzyme Nomenclature), preferably one or more carbohydrases including cellulolytic enzymes and hemicellulolytic enzymes, or combinations thereof. Further, protease, alpha-amylase, glucoamylase and/or the like may also be present during hydrolysis and/or fermentation as the lignocellulose-containing material may include some, e.g., starchy and/or proteinaceous material.

The enzyme(s) used for hydrolysis is(are) capable of directly or indirectly converting carbohydrate polymers into fermentable sugars, such as glucose and/or maltose, which can be fermented into a desired fermentation product, such as ethanol.

In a preferred embodiment the carbohydrase(s) has(have) cellulolytic and/or hemicellulolytic enzyme activity.

In a preferred embodiment hydrolysis is carried out using a cellulolytic enzyme preparation further comprising one or more polypeptides having cellulolytic enhancing activity. In a preferred embodiment the polypeptide(s) having cellulolytic enhancing activity is(are) of family GH61A origin. Examples of suitable and preferred cellulolytic enzyme preparations and polypeptides having cellulolytic enhancing activity are described in the "Cellulolytic Enzymes" section and "Cellulolytic Enhancing polypeptides" section below.

Suitable enzymes are described in the "Enzymes" section below.

Hemicellulose polymers can be broken down by hemicellulolytic enzymes and/or acid hydrolysis to release its five and six carbon sugar components. The six carbon sugars (hexoses), such as glucose, galactose, arabinose, and mannose, can readily be fermented to fermentation products such as ethanol, acetone, butanol, glycerol, citric acid, fumaric acid etc, by suitable fermenting organisms including yeast.

Yeast is the preferred fermenting organism for ethanol fermentation. Preferred are strains of *Saccharomyces*, especially strains of the species *Saccharomyces cerevisiae*, preferably strains which are resistant towards high levels of ethanol, i.e., up to, e.g., about 10, 12, 15 or 20 vol. % or more ethanol.

Enzymatic hydrolysis is preferably carried out in a suitable aqueous environment under conditions which can readily be determined by one skilled in the art. In a preferred embodiment hydrolysis is carried out at suitable, preferably optimal, conditions for the enzyme(s) in question.

Suitable process time, temperature and pH conditions can readily be determined by one skilled in the art. Preferably, hydrolysis is carried out at a temperature between 25 and 70° C., preferably between 40 and 60° C., especially around 50° C. The step is preferably carried out at a pH in the range from 3-8, preferably pH 4-6. Hydrolysis is typically carried out for between 12 and 96 hours, preferable 16 to 72 hours, more preferably between 24 and 48 hours.

Lignocellulose-Containing Material (Biomass)

Any suitable lignocellulose-containing material is contemplated in context of the present invention. Lignocellulose-containing material may be any material containing lignocellulose, in a preferred embodiment the lignocellulose-containing material contains at least 50 wt.-%, preferably at least 70 wt.-%, more preferably at least 90 wt.-% lignocellulose. It is to be understood that the lignocellulose-containing material may also comprise other constituents such as cellulosic material, such as cellulose, hemicellulose and may also comprise constituents such as sugars, such as fermentable sugars and/or un-fermentable sugars.

Ligno-cellulose-containing material is generally found, for example, in the stems, leaves, hulls, husks, and cobs of plants or leaves, branches, and wood of trees, Lignocellulosic material can also be, but is not limited to, herbaceous material, agricultural residues, forestry residues, municipal solid wastes, waste paper, and pulp and paper mill residues. It is understood herein that lignocellulose-containing material may be in the form of plant cell wall material containing lignin, cellulose, and hemi-cellulose in a mixed matrix.

In one embodiment the lignocellulose-containing material is selected from one or more of corn fiber, rice straw, pine wood, wood chips, poplar, bagasse, and paper and pulp processing waste.

Other examples of suitable lignocellulose-containing material include corn stover, corn cobs, hard wood such as poplar and birch, soft wood, cereal straw such as wheat straw, switch grass, *Miscanthus*, rice hulls, municipal solid waste (MSW), industrial organic waste, office paper, or mixtures thereof.

In a preferred embodiment the lignocellulose-containing material is corn stover or corn cobs. In another preferred embodiment, the lignocellulose-containing material is corn fiber. In another preferred embodiment, the lignocellulose-containing material is switch grass. In another preferred embodiment, the lignocellulose-containing material is bagasse.

Enzymes

Even if not specifically mentioned in context of a process of the invention, it is to be understood that the enzyme(s) is(are) used in an "effective amount".

Carbonic Anhydrases

According to the invention any carbonic anhydrase (CA) may be present during fermentation, in a preferred embodiment the carbonic anhydrase is of microbial origin, such as bacterial or fungal, such as yeast or filamentous fungus origin. In another embodiment the carbonic anhydrase is of mammalian or plant origin.

Carbonic anhydrases (also termed carbonate dehydratases) catalyze the inter-conversion between carbon dioxide and bicarbonate [$CO_2 + H_2O \leftrightarrows HCO_3^- + H^+$]. An example of a carbonic anhydrase (CA) includes the one discovered in bovine blood (Meldrum and Roughton, 1933, J Physiol 80: 113-142). Anhydrases are categorized in three distinct classes called the alpha-, beta- and gamma-class, and potentially a fourth class, the delta-class (Bacteria, Archaea, Eukarya; Tripp et al., 2001, J. Biol. Chem. 276: 48615-48618). For alpha-Cas more than 11 isozymes have been identified in mammals. Alpha-carbonic anhydrases are abundant in all mammalian tissues where they facilitate the removal of $CO_2$. Beta-Cas are ubiquitous in algae and plants where they provide for $CO_2$ uptake and fixation for photosynthesis. Gamma-Cas include one from Archaeon *Methanosarcina thermophila* strain TM-1 (Alber and Ferry, 1994, Proc. Natl. Acad. Sci. USA 91: 6909-6913) and the ones disclosed by Parisi et al., 2004, Plant Mol. Biol. 55: 193-207. In prokaryotes genes encoding all three CA classes have been identified, with the beta- and gamma-class predominating. Many prokaryotes contain carbonic anhydrase genes from more than one class or several genes of the same class (for review see Smith and Ferry, 2000, FEMS Microbiol. Rev. 24: 335-366: Tripp et al., 2001, J. Biol. Chem. 276: 48615-48618).

Mammalian-, plant- and prokaryotic carbonic anhydrases (alpha- and beta-class carbonis anhydrases) generally function at physiological temperatures (37° C.) or lower temperatures.

In another embodiment the carbonic anhydrase is the beta-class CA (Cab) from *Methanobacterium thermoautotrophicum* ΔH (Smith and Ferry, 1999, J Bacteriol 181: 6247-6253) or the gamma-class carbonic anhydrase (Cam) from *Methanosarcina thermophila* TM-1 (Alber and Ferry. 1994, Proc Natl Acad Sci USA 91: 6909-6913; Alber and Ferry, 1996, J. Bacteriol. 178: 3270-3274).

Other examples of carbonic anhydrases include carbonic anhydrases disclosed as SEQ ID NO: 2, SEQ ID NO: 4, SEQ ID NO: 6, SEQ ID NO: 8, SEQ ID NO: 10 or SEQ ID NO: 12 from *Bacillus clausii* or from *Bacillus clausii* KSM-K16 (NCBI acc. No. Q5WD44 or SEQ ID NO: 14) or from *Bacillus halodurans* (NCBI acc. No. Q9KFW1 or SEQ ID NO: 16) all disclosed in co-pending U.S. provisional application No. 60/887,386 from Novozymes, which is incorporated by reference.

In a preferred embodiment the carbonic anhydrase is derived from *Bacillus* sp. P203 deposited under accession # DSM 19153. The *Bacillus* sp. P203 carbonic anhydrase is disclosed and concerned in SEQ ID NO: 4 and Examples 8-10 in WO 2007/019859 (Novozymes A/S) which is hereby incorporated by reference.

According to a preferred embodiment of the invention the carbonic anhydrase is present or added to the fermentation medium in a concentration of 100-100,000 Units/g dry solids (DS), preferably 1,000-20,000 Units/g DS.

Alpha-Amylases

According to the invention any alpha-amylase may be used. In a preferred embodiment the alpha-amylase is an acid alpha-amylase, e.g., acid fungal alpha-amylase or acid bacterial alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

In one embodiment an alpha-amylase is present before and/or during fermentation. In a preferred embodiment the alpha-amylase is an alpha-amylase that has less than 70%, preferably less than 60%, more preferably less than 50%, even more preferably less than 40%, more preferably less than 30% residual activity left at a pH below 6, preferably pH 5, especially below pH 4.5 compared to its maximum activity (i.e., 100%). The residual activity of an alpha-amylase may be tested using the pH stability assay described in the "Materials & Methods" section.

Bacterial Alpha-Amylases

According to the invention the bacterial alpha-amylase is preferably derived from the genus Bacillus.

In a preferred embodiment the Bacillus alpha-amylase is derived from a strain of Bacillus licheniformis, Bacillus amyloliquefaciens, Bacillus subtilis or Bacillus stearothermophilus, but may also be derived from other Bacillus sp. Specific examples of contemplated alpha-amylases include the Bacillus licheniformis alpha-amylase shown in SEQ ID NO: 4 in WO 99/19467, the Bacillus amyloliquefaciens alpha-amylase SEQ ID NO: 5 in WO 99/19467 and the Bacillus stearothermophilus alpha-amylase shown in SEQ ID NO: 3 in WO 99/19467 (all sequences hereby incorporated by reference). In an embodiment the alpha-amylase may be an enzyme having a degree of identity of at least 60%, preferably at least 70%, more preferred at least 80%, even more preferred at least 90%, such as at least 95%, at least 96%, at least 97%, at least 98% or at least 99% to any of the sequences shown in SEQ ID NOS: 1, 2 or 3, respectively, in WO 99/19467.

The Bacillus alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or U.S. Pat. No. 6,187,576 (hereby incorporated by reference) and include Bacillus stearothermophilus alpha-amylase (BSG alpha-amylase) variants having a deletion of one or two amino acid in positions R179 to G182, preferably a double deletion disclosed in WO 1996/023873—see e.g., page 20, lines 1-10 (hereby incorporated by reference), preferably corresponding to delta(181-182) compared to the wild-type BSG alpha-amylase amino acid sequence set forth in SEQ ID NO:3 disclosed in WO 99/19467 or deletion of amino acids R179 and G180 using SEQ ID NO:3 in WO 99/19467 for numbering (which reference is hereby incorporated by reference). Even more preferred are Bacillus alpha-amylases, especially Bacillus stearothermophilus alpha-amylase, which have a double deletion corresponding to delta(181-182) and further comprise a N193F substitution (also denoted I181*+G182*+N193F) compared to the wild-type BSG alpha-amylase amino acid sequence set forth in SEQ ID NO:3 disclosed in WO 99/19467

Bacterial Hybrid Alpha-Amylases

A hybrid alpha-amylase specifically contemplated comprises 445 C-terminal amino acid residues of the Bacillus lichenifonnis alpha-amylase (shown in SEQ ID NO: 4 of WO 99/19467) and the 37 N-terminal amino acid residues of the alpha-amylase derived from Bacillus amyloliquefaciens (shown in SEQ ID NO: 5 of WO 99/19467), with one or more, especially all, of the following substitution:

G48A+T49I+G107A+H156Y+A181T+N190F+I201F+A209V+Q264S (using the Bacillus lichenifonnis numbering in SEQ ID NO: 4 of WO 99/19467). Also preferred are variants having one or more of the following mutations (or corresponding mutations in other Bacillus alpha-amylase backbones): H154Y, A181T, N190F, A209I/and Q264S and/or deletion of two residues between positions 176 and 179, preferably deletion of E178 and G179 (using the SEQ ID NO: 5 numbering of WO 99/19467).

In an embodiment the bacterial alpha-amylase is dosed in an amount of 0.0005-5 KNU per g DS, preferably 0.001-1 KNU per g DS, such as around 0.050 KNU per g DS.

Fungal Alpha-Amylases

Fungal alpha-amylases include alpha-amylases derived from a strain of the genus Aspergillus, such as, Aspergillus oryzae, Aspergillus niger and Aspergillis kawachii alpha-amylases.

A preferred acidic fungal alpha-amylase is a Fungamyl-like alpha-amylase which is derived from a strain of Aspergillus oryzae. According to the present invention, the term "Fungamyl-like alpha-amylase" indicates an alpha-amylase which exhibits a high identity, i.e. at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 10 in WO 96/23874.

Another preferred acid alpha-amylase is derived from a strain Aspergillus niger. In a preferred embodiment the acid fungal alpha-amylase is the one from Aspergillus niger disclosed as "AMYA_ASPNG" in the Swiss-prot/TeEMBL database under the primary accession no. P56271 and described in WO 89/01969 (Example 3—incorporated by reference). A commercially available acid fungal alpha-amylase derived from Aspergillus niger is SP288 (available from Novozymes A/S, Denmark).

Other contemplated wild-type alpha-amylases include those derived from a strain of the genera Rhizomucor and Meripilus, preferably a strain of Rhizomucor pusillus (WO 2004/055178 incorporated by reference) or Meripilus giganteus.

In a preferred embodiment the alpha-amylase is derived from Aspergillus kawachii and disclosed by Kaneko et al. J. Ferment. Bioeng 81292-298 (1996) "Molecular-cloning and determination of the nucleotide-sequence of a gene encoding an acid-stable alpha-amylase from Aspergillus kawachii,"; and further as EMBL: #AB008370.

The fungal alpha-amylase may also be a wild-type enzyme comprising a starch-binding domain (SBD) and an alpha-amylase catalytic domain (i.e., none-hybrid), or a variant thereof. In an embodiment the wild-type alpha-amylase is derived from a strain of Aspergillus kawachii.

Fungal Hybrid Alpha-Amylases

In a preferred embodiment the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in U.S. patent application No. 60/638,614, including Fungamyl variant with catalytic domain JA118 and *Athelia rolfsii* SBD (SEQ ID NO:100 in U.S. 60/638,614), *Rhizomucor pusillus* alpha-amylase with *Athelia rolfsii* AMG linker and SBD (SEQ ID NO:101 in U.S. 60/638,614), *Rhizomucor pusillus* alpha-amylase with *Aspergillus niger* glucoamylase linker and SBD (which is disclosed in Table 5 as a combination of amino acid sequences SEQ ID NO:20, SEQ ID NO:72 and SEQ ID NO:96 in U.S. application Ser. No. 11/316,535) or as V039 in Table 5 in WO 2006/069290, and *Meripilus giganteus* alpha-amylase with *Athelia rolfsii* glucoamylase linker and SBD (SEQ ID NO:102 in U.S. 60/638,614) Other specifically contemplated hybrid alpha-amylases are any of the ones listed in Tables 3, 4, 5, and 6 in Example 4 in U.S. application Ser. No. 11/316,535 and WO 2006/069290 (hereby incorporated by reference).

Other specific examples of contemplated hybrid alpha-amylases include those disclosed in U.S. Patent Publication no. 2005/0054071, including those disclosed in Table 3 on page 15, such as *Aspergillus niger* alpha-amylase with *Aspergillus kawachii* linker and starch binding domain.

Contemplated are also alpha-amylases which exhibit a high identity to any of above mention alpha-amylases, i.e., at least 70%, at least 75%, at least 80%, at least 85%, at least 90%, at least 95%, at least 96%, at least 97%, at least 98%, at least 99% or even 100% identity to the mature enzyme sequences.

An acid alpha-amylases may according to the invention be added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS, Commercial Alpha-Amylase Products Preferred commercial compositions comprising alpha-amylase include MYCOLASE™ from DSM (Gist Brocades), BAN™, TERMAMYL™ SC, FUNGAMYL™, LIQUOZYME™ X, LIQUOZYME™ SC and SAN™ SUPER, SAN™ EXTRA L (Novozymes A/S) and CLARASE™ L-40.000, DEX-LO™, SPEZYME® FRED-L, SPEZYME® HPA, SPEZYME® ALPHA, SPEZYME® XTRA, SPEZYME® AA, SPEZYME® DELTA AA, and GC358 (Genencor Int.), FUELZYME™-LF (Verenium Inc), and the acid fungal alpha-amylase sold under the trade name SP288 (available from Novozymes A/S, Denmark).

Carbohydrate-Source Generating Enzymes

The term "carbohydrate-source generating enzyme" includes glucoamylase (being glucose generators), beta-amylase and maltogenic amylase (being maltose generators) and also pullulanase and alpha-glucosidase. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Especially contemplated mixtures are mixtures of at least a glucoamylase and an alpha-amylase, especially an acid amylase, even more preferred an acid fungal alpha-amylase. The ratio between acid fungal alpha-amylase activity (AFAU) and glucoamylase activity (AGU) (i.e., AFAU per AGU) may in an embodiment be between 0.1 and 100, in particular between 2 and 50, such as in the range from 10-40.

Glucoamylases

A glucoamylase used according to the invention may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, EMBO J. 3 (5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem., 1991, 55 (4): 941-949), or variants or fragments thereof. Other *Aspergillus* glucoamylase variants include variants with enhanced thermal stability: G137A and G139A (Chen et al., 1996, Prot. Eng. 9, 499-505); D257E and D293E/Q (Chen et al., 1995, Prot. Eng. 8, 575-582); N182 (Chen et al. 1994, Biochem. J. 301, 275-281); disulphide bonds, A246C (Fierobe et al., 1996, Biochemistry, 35, 8698-8704; and introduction of Pro residues in position A435 and 5436 (Li et al. 1997, Protein Eng. 10, 1199-1204.

Other glucoamylases include *Athelia roifsii* (previously denoted *Corticium rolfsii*) glucoamylase (see U.S. Pat. No. 4,727,026 and (Nagasaka, Y. et al. (1998) "Purification and properties of the raw-starch-degrading glucoamylases from *Corticium rolfsii*, Appl Microbiol Biotechnol 50.323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215).

Bacterial glucoamylases contemplated include glucoamylases from the genus *Clostridium*, in particular *C. thermoamylolyticum* (EP 135,138), and *C. thermohydrosulfuricum* (WO 86/01831) and *Trametes cingulata, Pachykytospora papyracea*; and *Leucopaxillus giganteus* all disclosed in WO 2006/069289: or *Peniphora rufomarginata* disclosed in PCT/US2007/066618; or a mixture thereof. Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference).

Contemplated are also glucoamylases which exhibit a high identity to any of above mention glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above.

Commercially available compositions comprising glucoamylase include AMG 200L; AMG 300 L; SAN™ SUPER, SAN™ EXTRA L. SPIRIZYME™ PLUS, SPIRIZYME™ FUEL, SPIRIZYME™ B4U, SPIRIZYME™ ULTRA and AMG™ E (from Novozymes A/S); OPTIDEX™ 300, GC480, GC147 (from Genencor Int); AMIGASET™ and AMIGASE™ PLUS (from DSM); G-ZYME® G900, G-ZYME®, G-ZYME® 480 ETHANOL, DISTILLASE® L-400, DISTILLASE® L-500, DISTILLASE® VHP, and G990 ZR (from Genencor Int.)

Glucoamylases may in an embodiment be added in an amount of 0.0001-20 AGU/g DS, preferably 0.001-10 AGU/g DS, especially between 0.01-5 AGU/g DS, such as 0.1-2 AGU/g DS.

Beta-Amylases

A beta-amylase (E.C 3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (W. M. Fogarty and C. T. Kelly, Progress in Industrial Microbiology, vol. 15, pp. 112-115, 1979). These beta-amylases are characterized by having optimum temperatures in the range from 40° C. to 65° C. and optimum pH in the range from 4.5 to 7. A commercially available beta amylase from barley is NOVOZYM™ WBA from Novozymes A/5, Denmark and SPEZYME™ BBA 1500 from Genencor Int., USA.

Maltogenic Amylases

The amylase may also be a maltogenic alpha-amylase. A "maltogenic alpha-amylase" (glucan 1,4-alpha-maltohydrolase, EC. 3.2, 1.133) is able to hydrolyze amylose and amylopectin to maltose in the alpha-configuration. A maltogenic amylase from *Bacillus stearothermophilus* strain NCIB 11837 is commercially available from Novozymes A/S, Maltogenic alpha-amylases are described in U.S. Pat. Nos. 4,598, 048, 4,604,355 and 6,162,628, which are hereby incorporated by reference.

The maltogenic amylase may in a preferred embodiment be added in an amount of 0.05-5 mg total protein/gram DS or 0.05-5 MANU/g DS.

The carbohydrate-source generating enzyme may be any carbohydrate-source generating enzyme, including the ones listed in the "Carbohydrate-Source Generating Enzymes" section above. In a preferred embodiment the carbohydrate-source generating enzyme is a glucoamylase. In an preferred embodiment the glucoamylase is selected from the group derived from a strain of *Aspergillus*, preferably *Aspergillus niger* or *Aspergillus awamori*, a strain of *Talaromyces*, especially *Talaromyces emersonii*; or a strain of *Athelia*, especially *Athelia rolfsii*, a strain of *Trametes*, preferably *Trametes cingulata*; a strain of the genus *Pachykytospora*, preferably a strain of *Pachykytospora papyracea*; or a strain of the genus *Leucopaxillus*, preferably *Leucopaxillus giganteus*; or a strain of the genus *Peniophora*, preferably a strain of the species *Peniophora ruformarginata*; or a mixture thereof.

The alpha-amylase may be any alpha-amylase, including the ones mentioned in the "Alpha-Amylases" section above. In a preferred embodiment the alpha-amylase is an acid alpha-amylase, especially an acid fungal alpha-amylase. In a preferred embodiment the alpha-amylase is selected from the group of fungal alpha-amylases. In a preferred embodiment the alpha-amylase is derived from the genus *Aspergillus*, especially a strain of *A. niger, A. oryzae, A. awamori,* or *Aspergillus kawachii*, or of the genus *Rhizomucor*, preferably a strain the *Rhizomucor pusillus*, or the genus *Meripitus*, preferably a strain of *Meripilus giganteus*.

The ratio between glucoamylase activity (AGU) and fungal alpha-amylase activity (FAU-F) (the ratio of AGU per FAU-F) may in an embodiment of the invention be between 0.1 and 100 AGU/FAU-F, in particular between 2 and 50 AGU/FAU-F, such as in the range from 10-40 AGU/FAU-F. The ratio of acid alpha-amylase to glucoamylase is in the range between 0.3 and 5.0 AFAU/AGU. Above composition of the invention is suitable for use in a process for producing fermentation products, such as ethanol, of the invention.

Cellulolytic Activity

The term "cellulolytic activity" as used herein are understood as comprising enzymes having cellobiohydrolase activity (EC 3.2.1.91), e.g., cellobiohydrolase I and cellobiohydrolase II, as well as endo-glucanase activity (EC 3.2.1.4) and beta-glucosidase activity (EC 3.2.1.21).

At least three categories of enzymes are important for converting cellulose into fermentable sugars: endo-glucanases (EC 3.2.1.4) that cut the cellulose chains at random; cellobiohydrolases (EC 3.2.1.91) which cleave cellobiosyl units from the cellulose chain ends and beta-glucosidases (EC 3.2.1.21) that convert cellobiose and soluble cellodextrins into glucose. Among these three categories of enzymes involved in the biodegradation of cellulose, cellobiohydrolases seems to be the key enzymes for degrading native crystalline cellulose.

The cellulolytic activity may, in a preferred embodiment, be in the form of a preparation of enzymes of fungal origin, such as from a strain of the genus *Trichoderma*, preferably a strain of *Trichoderma reesei*; a strain of the genus *Humicola*, such as a strain of *Humicola insolens*; or a strain of *Chrysosporium*, preferably a strain of *Chrysosporium lucknowense*.

In preferred embodiment the cellulolytic enzyme preparation contains one or more of the following activities: cellulase, hemicellulase, cellulolytic enzyme enhancing activity, beta-glucosidase activity, endoglucanase, cellobiohydrolase, or xylose isomerase.

In a preferred embodiment the cellulase may be a composition as defined in PCT/US2008/065417, which is hereby incorporated by reference. In one embodiment the cellulolytic enzyme preparation comprising a polypeptide having cellulolytic enhancing activity, preferably a family GH61A polypeptide, preferably the one disclosed in WO 2005/074656 (Novozymes) The cellulolytic enzyme preparation may further comprise a beta-glucosidase, such as a beta-glucosidase derived from a strain of the genus *Trichoderma*, *Aspergillus* or *Penicillium*, including the fusion protein having beta-glucosidase activity disclosed in WO 2008/057637, in a preferred embodiment the cellulolytic enzyme preparation may also comprises a CBH II enzyme, preferably *Thielavia terrestris* cellobiohydrolase II CEL6A In another preferred embodiment the cellulolytic enzyme preparation may also comprise cellulolytic enzymes, preferably one derived from *Trichoderma reesei* or *Humicola insolens*.

The cellulolytic enzyme preparation may also comprising a polypeptide having cellulolytic enhancing activity (GH61A) disclosed in WO 2005/074656: a beta-glucosidase (fusion protein disclosed in WO 2008/057637) and cellulolytic enzymes derived from *Trichoderma reesei*.

In an embodiment the cellulolytic enzyme is the commercially available product CELLUCLAST® 1.5L or CELLUZYME™ available from Novozymes A/S, Denmark or ACCELERASE™ 1000 (from Genencor inc., USA).

A cellulolytic enzyme may be added for hydrolyzing the pre-treated lignocellulose-containing material. The cellulolytic enzyme may be dosed in the range from 0.1-100 FPU per gram total solids (TS), preferably 05-50 FPU per gram TS, especially 1-20 FPU per gram TS. In another embodiment at least 0.1 mg cellulolytic enzyme per gram total solids (TS), preferably at least 3 mg cellulolytic enzyme per gram TS, such as between 5 and 10 mg cellulolytic enzyme(s) per gram TS is(are) used for hydrolysis.

Endoglucanases (EG)

The term "endoglucanase" means an endo-1,4-(1,3;1,4)-beta-D-glucan 4-glucanohydrolase (E.C. No. 3.2.1.4), which catalyses endo-hydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity may be determined using carboxymethyl cellulose (CMC) hydrolysis according to the procedure of Ghose, 1987, *Pure and Appl. Chem.* 59: 257-268.

In a preferred embodiment endoglucanases may be derived from a strain of the genus *Trichoderma*, preferably a strain of *Trichoderma reesei*; a strain of the genus *Humicola*, such as a strain of *Humicola insolens*; or a strain of *Chrysosporium*, preferably a strain of *Chrysosporium lucknowense*.

Cellobiohydrolases (CBH)

The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain.

Examples of cellobiohydrolases are mentioned above including CBH I and CBH II from *Trichoderma reesei*; *Humicola insolens* and CBH II from *Thielavia terrestris* cellobiohydrolase (CELL6A)

Cellobiohydrolase activity may be determined according to the procedures described by Lever et al., 972, *Anal. Biochem.* 47: 273-279 and by van Tilbeurgh at, 1982, *FEBS Letters* 149: 152-156: van Tilbeurgh and Claeyssens, 1985, *FEBS Letters* 187: 283-288. The Lever et al. method is suitable for assessing hydrolysis of cellulose in corn stover and the method of van Tilbeurgh et al. is suitable for determining the cellobiohydrolase activity on a fluorescent disaccharide derivative.

Beta-Glucosidases

One or more beta-glucosidases may be present during hydrolysis.

The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 μmole of p-nitrophenol produced per minute at 50° C., pH 5 from 4 mM p-nitrophenyl-beta-D-glucopyranoside as substrate in 100 mM sodium citrate, 0.01% TWEEN® 20.

In a preferred embodiment the beta-glucosidase is of fungal origin, such as a strain of the genus *Trichoderma*, *Aspergillus* or *Penicillium*. In a preferred embodiment the beta-glucosidase is a derived from *Trichoderma reesei*, such as the beta-glucosidase encoded by the bgl1 gene (see FIG. 1 of EP 562003). In another preferred embodiment the beta-glucosidase is derived from *Aspergillus oryzae* (recombinantly produced in *Aspergillus oryzae* according to WO 02/095014), *Aspergillus fumigatus* (recombinantly produced in *Aspergillus oryzae* according to Example 22 of WO 02/095014) or *Aspergillus niger* (1981, J. Appl. Vol 3, pp 157-163).

Hemicellulolytic Enzymes

According to the invention the pre-treated lignocellulose-containing material may further be subjected to one or more hemicellulolytic enzymes, e.g., one or more hemicellulases.

Hemicellulose can be broken down by hemicellulases and/or acid hydrolysis to release its five and six carbon sugar components.

In an embodiment of the invention the lignocellulose derived material may be treated with one or more hemicellulases.

Any hemicellulase suitable for use in hydrolyzing hemicellulose, preferably into xylose, may be used. Preferred hemicellulases include xylanases, arabinofuranosidases, acetyl xylan esterase, feruloyl esterase, glucuronidases; endo-galactanase; mannases, endo or exo arabinases, exo-galactanses, and mixtures of two or more thereof. Preferably, the hemicellulase for use in the present invention is an exo-acting hemicellulase, and more preferably, the hemicellulase is an exo-acting hemicellulase which has the ability to hydrolyze hemicellulose under acidic conditions of below pH 7, preferably pH 3-7. An example of hemicellulase suitable for use in the present invention includes VISCOZYME™ (available from Novozymes A/S, Denmark).

In an embodiment the hemicellulase is a xylanase. In an embodiment the xylanase may preferably be of microbial origin, such as of fungal origin (e.g., *Trichoderma, Meripilus, Humicola, Aspergillus, Fusarium*) or from a bacterium (e.g., *Bacillus*). In a preferred embodiment the xylanase is derived from a filamentous fungus, preferably derived from a strain of *Aspergillus*, such as *Aspergillus aculeatus*; or a strain of *Humicola*, preferably *Humicola lanuginosa*. The xylanase may preferably be an endo-1,4-beta-xylanase, more preferably an endo-1,4-beta-xylanase of GH10 or GH11. Examples of commercial xylanases include SHEARZYME™ and BIOFEED WHEAT™ from Novozymes A/S, Denmark.

The hemicellulase may be added in an amount effective to hydrolyze hemicellulose, such as, in amounts from about 0.001 to 0.5 wt.-% of total solids (TS), more preferably from about 0.05 to 0.5 wt.-% of TS.

Xylanases may be added in amounts of 0.001-1.0 g/kg DM (dry matter) substrate, preferably in the amounts of 0.005-0.5 g/kg DM substrate, and most preferably from 0.05-0.10 g/kg DM substrate.

Xylose Isomerases

Xylose isomerases (D-xylose ketoisomerase) (E.C. 5.3.1.5.) are enzymes that catalyze the reversible isomerization reaction of D-xylose to D-xylulose. Some xylose isomerases also convert the reversible isomerization of D-glucose to D-fructose. Therefore, xylose isomerase is sometimes referred to as "glucose isomerase."

A xylose isomerase used in a method or process of the invention may be any enzyme having xylose isomerase activity and may be derived from any sources, preferably bacterial or fungal origin, such as filamentous fungi or yeast. Examples of bacterial xylose isomerases include the ones belonging to the genera *Streptomyces*, *Actinoplanes*, *Bacillus* and *Flavobacterium*, and *Thermotoga*, including *T. neapalitana* (Vieille et al., 1995, Appl. Environ. Microbial. 61 (5), 1867-1875) and *T. maritime*.

Examples of fungal xylose isomerases are derived species of *Basidiomycetes*.

A preferred xylose isomerase is derived from a strain of yeast genus *Candida*, preferably a strain of *Candida boidinii*, especially the *Candida boidinii* xylose isomerase disclosed by, e.g., Vongsuvanlert et al., 1988, Agric. Biol. Chem., 52(7): 1817-1824. The xylose isomerase may preferably be derived from a strain of *Candida boidinii* (Kloeckera 2201), deposited as DSM 70034 and ATCC 48180, disclosed in Ogata et al., Agric. Biol. Chem., Vol. 33, p. 1519-1520 or Vongsuvanlert et al., 1988, Agric. Biol. Chem., 52(2), p. 1519-1520.

In one embodiment the xylose isomerase is derived from a strain of *Streptomyces*, e.g., derived from a strain of *Streptomyces murinus* (U.S. Pat. No. 4,687,742): *S. flavovirens, S. albus, S. achromogenus, S. echinatus, S. wedmorensis* all disclosed in U.S. Pat. No. 3,616,221. Other xylose isomerases are disclosed in U.S. Pat. No. 3,622,463, U.S. Pat. No. 4,351, 903, U.S. Pat. No. 4,137,126, U.S. Pat. No. 3,625,828, HU patent no. 12,415, DE patent 2,417,642, JP patent no. 69,28, 473, and WO 2004/044129 each incorporated by reference herein.

The xylose isomerase may be either in immobilized or liquid form. Liquid form is preferred.

Examples of commercially available xylose isomerases include SWEETZYME™ T from Novozymes A/S, Denmark.

The xylose isomerase is added to provide an activity level in the range from 0.01-100 IGIU per gram total solids.

Cellulolytic Enhancing Activity

The term "cellulolytic enhancing activity" is defined herein as a biological activity that enhances the hydrolysis of a lignocellulose derived material by proteins having cellulolytic activity. For purposes of the present invention, cellulolytic enhancing activity is determined by measuring the increase in reducing sugars or in the increase of the total of cellobiose and glucose from the hydrolysis of a lignocellulose derived material, e.g., pre-treated lignocellulose-containing material by cellulolytic protein under the following conditions: 1-50 mg of total protein/g of cellulose in PCS (pre-treated corn stover), wherein total protein is comprised of 80-99.5% w/w cellulolytic protein/g of cellulose in PCS and 0.5-20% w/w protein of cellulolytic enhancing activity for 1-7 day at 50° C. compared to a control hydrolysis with equal total protein loading without cellulolytic enhancing activity (1-50 mg of cellulolytic protein/g of cellulose in PCS).

The polypeptides having cellulolytic enhancing activity enhance the hydrolysis of a lignocellulose derived material catalyzed by proteins having cellulolytic activity by reducing the amount of cellulolytic enzyme required to reach the same degree of hydrolysis preferably at least 0.1-fold, more at least 0.2-fold, more preferably at least 0.3-fold, more preferably at least 0.4-fold, more preferably at least 0.5-fold, more preferably at least 1-fold, more preferably at least 3-fold, more preferably at least 4-fold, more preferably at least 5-fold, more preferably at least 10-fold, more preferably at least 20-fold, even more preferably at least 30-fold, most preferably at least 50-fold, and even most preferably at least 100-fold.

In a preferred embodiment the hydrolysis and/or fermentation is carried out in the presence of a cellulolytic enzyme in combination with a polypeptide having enhancing activity. In a preferred embodiment the polypeptide having enhancing activity is a family GH61A polypeptide. WO 2005/074647 discloses isolated polypeptides having cellulolytic enhancing activity and polynucleotides thereof from *Thielavia terrestris*, WO 2005/074656 discloses an isolated polypeptide having cellulolytic enhancing activity and a polynucleotide thereof from *Thermoascus aurantiacus*. U.S. Published Application Serial No. 2007/0077630 discloses an isolated polypeptide having cellulolytic enhancing activity and a polynucleotide thereof from *Trichoderma reesei*.

Proteases

A protease may be added during hydrolysis in step ii), fermentation in step iii) or simultaneous hydrolysis and fermentation. The protease may be any protease. In a preferred embodiment the protease is an acid protease of microbial origin, preferably of fungal or bacterial origin. An acid fungal protease is preferred, but also other proteases can be used.

Suitable proteases include microbial proteases, such as fungal and bacterial proteases. Preferred proteases are acidic proteases, i.e., proteases characterized by the ability to hydrolyze proteins under acidic conditions below pH 7.

Contemplated acid fungal proteases include fungal proteases derived from *Aspergillus, Mucor, Rhizopus, Candida, Carlolus, Endothia, Enthomophtra, Irpex, Sclerotium* and *Torulopsis*. Especially contemplated are proteases derived from *Aspergillus niger* (see, e.g., Koaze et al., 1964, Agr. Biol. Chem. Japan, 28, 216). *Aspergillus saitoi* (see, e.g., Yoshida, 1954, J. Agr. Chem. Soc. Japan, 28, 66), *Aspergillus awamari* (Hayashida et al., (1977) Agric. Biol. Chem., 42(5), 927-933, *Aspergillus aculeatus* (WO 95/02044), or *Aspergillus oryzae*, such as the pepA protease; and acidic proteases from *Mucor pusillus* or *Mucor miehei*.

Contemplated are also neutral or alkaline proteases, such as a protease derived from a strain of *Bacillus*. A particular protease contemplated for the invention is derived from *Bacillus amyloliquefaciens* and has the sequence obtainable at Swissprot as Accession No, P06832. Also contemplated are the proteases having at least 90% identity to amino acid sequence obtainable at Swissprot as Accession No. P06832 such as at least 92%, at least 95%, at least 96%, at least 97%, at least 98%, or particularly at least 99% identity.

Further contemplated are the proteases having at least 90% identity to amino acid sequence disclosed as SEQ. ID. NO:1 in the WO 2003/048353 such as at 92%, at least 95%, at least 96%, at least 97%, at least 98%, or particularly at least 99% identity.

Also contemplated are papain-like proteases such as proteases within E.C. 3.4.22.* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

In an embodiment the protease is a protease preparation derived from a strain of *Aspergillus*, such as *Aspergillus oryzae*. In another embodiment the protease is derived from a strain of *Rhizomucor*, preferably *Rhizomucor mehei*. In another contemplated embodiment the protease is a protease preparation, preferably a mixture of a proteolytic preparation derived from a strain of *Aspergillus*, such as *Aspergillus oryzae*, and a protease derived from a strain of *Rhizomucor*, preferably *Rhizomucor mehei*.

Aspartic acid proteases are described in, for example, Hand-book of Proteolytic Enzymes, Edited by A. J. Barrett, N. D. Rawlings and J. F. Woessner, Aca-demic Press, San Diego, 1998, Chapter 270). Suitable examples of aspartic acid protease include, e.g., those disclosed in R. M. Berka et al. Gene, 96, 313 (1990)); (R. M. Berka et al. Gene. 125, 195-198 (1993)); and Gomi et al. Biosci. Biotech. Biochem, 57, 1095-1100 (1993), which are hereby incorporated by reference.

Commercially available products include ALCALASE®, ESPERASE™, FLAVOURZYME™, PROMIX™, NEUTRASE®, RENNILASE®, NOVOZYM™ FM 2.0L, and NOVOZYM™ 50006 (available from Novozymes A/S, Denmark) and GC106™ and SPEZYME™ FAN from Genencor int., Inc., USA.

The protease may be present in an amount of 0.0001-1 mg enzyme protein per g DS, preferably 0.001 to 0.1 mg enzyme protein per g DS. Alternatively, the protease may be present in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

Compositions

In this aspect the invention relates to a composition comprising one or more carbonic anhydrases and one or more carbohydrases. In a preferred embodiment the carbohydrase is an alpha-amylase. In a preferred embodiment the alpha-amylase is an acid amylase or fungal alpha-amylase, preferably an acid fungal alpha-amylase.

In a preferred embodiment the composition comprises enzymes selected from the group consisting cellulolytic enzymes, such as cellulases, and/or hemicellulolytic enzymes, such as hemicellulases. The composition may also comprise carbohydrate-source generating enzymes, such as especially glucoamylases, beta-amylases, maltogenic amylases, pullulanases, alpha-glucosidases, or a mixture thereof.

Examples of contemplated enzymes can be found above in "Enzymes" section above.

Uses

In this aspect the invention relates to the use of carbonic anhydrase for controlling pH fluctuation during fermentation. In a preferred embodiment the fermentation is a process of the invention. The invention also relates to the use of carbonic anhydrase for improving yeast fermentation product yields and fermentation rate.

Transgenic Plant Materials

In this final aspect the invention relates to transgenic plant material transformed with one or more carbonic anhydrase genes.

In another embodiment the invention relates to a transgenic plant capable of expression one or more carbonic anhydrases in increased amounts compared to corresponding unmodified plant material.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

Materials & Methods

Materials:

Carbonic Anhydrase (CA): Carbonic anhydrase derived from *Bacillus clausii* KSM-K16 (Uniprot acc. No. Q5WD44).
Glucoamylase (AMG A): Glucoamylase derived from *Trametes cingulata* disclosed in SEQ ID NO: 2 in WO 2006/069289 and available from Novozymes A/S.
Alpha-Amylase (AA 1): Hybrid alpha-amylase consisting of *Rhizomucor pusillus* alpha-amylase with *Aspergillus niger* glucoamylase linker and SBD disclosed as V039 in Table 5 in WO 2006/069290 (Novozymes A/S).
Yeast: RED STAR™ available from Red Star/Lesaffre, USA Methods:

Identity

The relatedness between two amino acid sequences or between two nucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Detection of Carbonic Anhydrase Activity (Wilbur Units)

The test for the detection of carbonic anhydrase was described by Wilbur, 1948, J. Biol. Chem., 176: 147-154. The set up is based on the pH change of the assay mixture due to the formation of bicarbonate from carbon dioxide as given in equation 1: $[CO_2+H_2O \rightarrow HCO_3^- +H^+]$.

The activity assay used in this study was derived from the procedure of Chirica et al., 2001, Biochim. Biophys. Acta, 2005, 1544(1-2): 55-63. A solution containing approximately 60 to 70 mM $CO_2$ was prepared by bubbling $CO_2$ into 100 ml distilled water using the tip of a syringe approximately 45 min to 1 h prior to the assay. The $CO_2$ solution was chilled in an ice-water bath. To test for the presence of carbonic anhydrase, 2 ml of 25 mM Tris, pH 8.3 (containing sufficient bromothymol blue to give a distinct and visible blue color) were added to two 13×100 mm test tubes chilled in an ice bath. To one tube, 10 to 50 microliters of the enzyme containing solution (e.g. culture broth or purified enzyme) was added, and an equivalent amount of buffer was added to the second tube to serve as a control. Using a 2 ml syringe and a long cannula, 2 ml of $CO_2$ solution was added very quickly and smoothly to the bottom of each tube. Simultaneously with the addition of the $CO_2$ solution, a stopwatch was started. The time required for the solution to change from blue to yellow was recorded (transition point of bromothymol blue is pH 6-7.6). The production of hydrogen ions during the $CO_2$ hydration reaction lowers the pH of the solution until the color transition point of the bromothymol blue is reached. The time required for the color change is inversely related to the quantity of carbonic anhydrase present in the sample. The tubes must remain immersed in the ice bath for the duration of the assay for results to be reproducible. Typically, the uncatalyzed reaction (the control) takes approximately 2 min for the color change to occur, whereas the enzyme catalyzed reaction is complete in 5 to 15 s, depending upon the amount of enzyme added. Detecting the color change is somewhat subjective but the error for triple measurements was in the range of 0 to 1 sec difference for the catalyzed reaction. One unit is defined after Wilbur [$1 U=(1/t_c)-(1/t_u)\times 1000$] where U is units and $t_c$ and $t_u$ represent the time in seconds for the catalyzed and uncatalyzed reaction, respectively (Wilbur, 1948. J. Biol. Chem. 176: 147-154).

Glucoamylase Activity

Glucoamylase activity may be measured in AGI units or in Glucoamylase Units (AGU).

Glucoamylase Activity (AGI)

Glucoamylase (equivalent to amyloglucosidase) converts starch into glucose. The amount of glucose is determined here by the glucose oxidase method for the activity determination. The method described in the section 76-11 Starch-Glucoamylase Method with Subsequent Measurement of Glucose with Glucose Oxidase in "Approved methods of the American Association of Cereal Chemists". Vol. 1-2 AACC, from American Association of Cereal Chemists (2000); ISBN: 1-891127-12-8.

One glucoamylase unit (AGI) is the quantity of enzyme which will form 1 micro mole of glucose per minute under the standard conditions of the method.

Standard Conditions/Reaction Conditions

| | |
|---|---|
| Substrate: | Soluble starch, concentration approx. 16 g dry matter/L. |
| Buffer: | Acetate, approx. 0.04 M, pH = 4.3 |
| pH: | 4.3 |
| Incubation temperature: | 60° C. |
| Reaction time: | 15 minutes |
| Termination of the reaction: | NaOH to a concentration of approximately 0.2 g/L (pH ~9) |
| Enzyme concentration: | 0.15-0.55 AAU/mL. |

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

AMG incubation:

| Substrate: | maltose 23.2 mM |
|---|---|
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |

Color reaction

| GlucDH: | 430 U/L |
|---|---|
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution, initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Acid Alpha-Amylase Activity (AFAU)

When used according to the present invention the activity of an acid alpha-amylase may be measured in AFAU (Acid Fungal Alpha-amylase Units). Alternatively, activity of acid alpha-amylase may be measured in AAU (Acid Alpha-amylase Units).

The acid alpha-amylase activity can be measured in AAU (Acid Alpha-Amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

Standard Conditions/Reaction Conditions:

| Substrate: | Soluble starch. Concentration approx. 20 g DS/L. |
|---|---|
| Buffer: | Citrate, approx. 0.13 M, pH = 4.2 |
| Iodine solution: | 40.176 g potassium iodide + 0.088 g iodine/L |
| City water | 15°~20° dH (German degree hardness) |
| pH: | 4.2 |
| Incubation temperature: | 30° C. |
| Reaction time: | 11 minutes |
| Wavelength: | 620 nm |
| Enzyme concentration: | 0.13-0.19 AAU/mL |
| Enzyme working range: | 0.13-0.19 AAU/mL |

The starch should be Lintner starch, which is a thin-boiling starch used in the laboratory as colorimetric indicator. Lintner starch is obtained by dilute hydrochloric acid treatment of native starch so that it retains the ability to color blue with iodine. Further details can be found in EP 0140410 B2, which disclosure is herein incorporated by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

$$\text{STARCH + IODINE} \xrightarrow[t = 23 \text{ sec.}]{\text{ALPHA-AMYLASE}} \text{DEXTRINS + OLIGOSACCHARIDES}$$

$\lambda = 590$ nm
blue/violet decoloration

Standard Conditions/Reaction Conditions:

| | |
|---|---|
| Substrate: | Soluble starch, approx. 0.17 g/L |
| Buffer: | Citrate, approx. 0.03 M |
| Iodine (I2): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available on request from Novozymes A/S, Denmark, which folder is hereby included by reference.

Measurement of Cellulase Activity Using Filter Paper Assay (FPU assay)

1. Source of Method
1.1 The method is disclosed in a document entitled "Measurement of Cellulase Activities" by Adney, B. and Baker, J. 1996. Laboratory Analytical Procedure, LAP-006, National Renewable Energy Laboratory (NREL). It is based on the IUPAC method for measuring cellulase activity (Ghose, T. K., Measurement of Cellulose Activities, Pure & Appl. Chem. 59, pp. 257-268, 1987.
2. Procedure
2.1 The method is carried out as described by Adney and Baker, 1996, supra, except for the use of a 96 well plates to read the absorbance values after color development, as described below.
2.2 Enzyme Assay Tubes:
2.2.1 A rolled filter paper strip (#1 Whatman; 1×6 cm; 50 g is added to the bottom of a test tube (13×100 mm).
2.2.2 To the tube is added 1.0 mL of 0.05 M Na-citrate buffer (pH 4.80).
2.2.3 The tubes containing filter paper and buffer are incubated 5 min. at 50° C. (±0.1° C.) in a circulating water bath.
2.2.4 Following incubation, 0.5 mL of enzyme dilution in citrate buffer is added to the tube. Enzyme dilutions are designed to produce values slightly above and below the target value of 2.0 mg glucose.
2.2.5 The tube contents are mixed by gently vortexing for 3 seconds.
2.2.6 After vortexing, the tubes are incubated for 60 mins. at 50° C. (±0.1° C.) in a circulating water bath.
2.2.7 Immediately following the 60 min, incubation, the tubes are removed from the water bath, and 3.0 mL of DNS reagent is added to each tube to stop the reaction. The tubes are vortexed 3 seconds to mix.
2.3 Blank and Controls
2.3.1 A reagent blank is prepared by adding 1.5 mL of citrate buffer to a test tube.
2.3.2 A substrate control is prepared by placing a rolled filter paper strip into the bottom of a test tube, and adding 1.5 mL of citrate buffer.
2.3.3 Enzyme controls are prepared for each enzyme dilution by mixing 1.0 mL of citrate buffer with 0.5 mL of the appropriate enzyme dilution.
2.3.4 The reagent blank, substrate control, and enzyme controls are assayed in the same manner as the enzyme assay tubes, and done along with them.
2.4 Glucose Standards
2.4.1 A 100 mL stock solution of glucose (10.0 mg/mL) is prepared, and 5 mL aliquots are frozen. Prior to use, aliquots are thawed and vortexed to mix 2.4.2 Dilutions of the stock solution are made in citrate buffer as follows:
G1=1.0 mL stock+0.5 mL buffer=6.7 mg/mL=3.3 mg/0.5 mL
G2=0.75 mL stock+0.75 mL buffer=5.0 mg/mL=2.5 mg/0.5 mL
G3=0.5 mL stock+1.0 mL buffer=3.3 mg/mL=1.7 mg/0.5 mL
G4=0.2 mL stock+0.8 mL buffer=2.0 mg/mL=1.0 mg/0.5 mL
2.4.3 Glucose standard tubes are prepared by adding 0.5 mL of each dilution to 1.0 mL of citrate buffer.
2.4.4 The glucose standard tubes are assayed in the same manner as the enzyme assay tubes, and done along with them.
2.5 Color Development
2.5.1 Following the 60 min. incubation and addition of DNS, the tubes are all boiled together for 5 mins. in a water bath.
2.5.2 After boiling, they are immediately cooled in an ice/water bath.
2.5.3 When cool, the tubes are briefly vortexed, and the pulp is allowed to settle. Then each tube is diluted by adding 50 microL from the tube to 200 microL of $ddH_2O$ in a 96-well plate. Each well is mixed, and the absorbance is read at 540 nm.
2.6 Calculations (Examples are Given in the NREL Document)
2.6.1 A glucose standard curve is prepared by graphing glucose concentration (mg/0.5 mL) for the four standards (G1-G4) vs. $A_{540}$. This is fitted using a linear regression (Prism Software), and the equation for the line is used to determine the glucose produced for each of the enzyme assay tubes.
2.6.2 A plot of glucose produced (mg/0.5 mL) vs. total enzyme dilution is prepared, with the Y-axis (enzyme dilution) being on a log scale.
2.6.3 A line is drawn between the enzyme dilution that produced just above 2.0 mg glucose and the dilution that produced just below that. From this line, it is determined the enzyme dilution that would have produced exactly 2.0 mg of glucose.
2.6.4 The Filter Paper Units/mL (FPU/mL) are calculated as follows:
FPU/mL 0.37/enzyme dilution producing 2.0 mg glucose Protease Assay Method—AU(RH)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU-RH) is defined as the amount of enzyme which under standard conditions (i.e. 25° C., pH 5.5 and 10 min, reaction time) digests hemoglobin at an initial rate such that there is liberated per minute an amount of TCA soluble product which gives the same color with phenol reagent as one milliequivalent of tyrosine.

The AU(RH) method is described in EAL-SM-0350 and is available from Novozymes A/S Denmark on request.

Protease Assay Method (LAPU)

1 Leucine Amino Peptidase Unit (LAPU) is the amount of enzyme which decomposes 1 microM substrate per minute at the following conditions: 26 mM of L-leucine-p-nitroanilide as substrate, 0.1 M Tris buffer (pH 8.0), 37° C., 10 minutes reaction time.

LAPU is described in EB-SM-0298.02/01 available from Novozymes A/S Denmark on request.

Determination of Maltogenic Amylase Activity (MANU)

One MANU (Maltogenic Amylase Novo Unit) may be defined as the amount of enzyme required to release one micro mole of maltose per minute at a concentration of 10 mg of maltotriose (Sigma M 8378) substrate per ml of 0.1 M citrate buffer, pH 5.0 at 37° C. for 30 minutes.

Assay Method for pH Stability of Alpha-Amylase

Alpha-amylase is diluted to appropriate concentration of 0.03 AFAU/ml. The assay is carried out in a micro-plate.

10 microL of diluted enzyme is added to 6 microL of stock buffer (0.5 M) with different pH, ranging from pH 2.5 to 8.0 and added 67 microL of MilliQ water to final buffer concentration of 0.0375 M. The mixture is incubated at 37° C. for 2 hours. Subsequently the residual activity of the enzyme in question is assayed by adding 80 microL of starch working solution (final concentration: 0.35 gil gelatinized starch; 50 mM NaAc, pH 4.0; 0.1 M NaCl; 3 mM $CaCl_2$). The reaction is carried out at 37° C. for 2 minutes with shaking in the microplate reader and 40 microL of freshly prepared iodine working solution (final concentration: 0.2% KI; 0.02% iodine). The mixture is further incubated at 37° C. for 1 minute without shaking in the microplate reader. Absorbance at 590 nm is taken. pH stability is determined.

EXAMPLES

Example 1

Effect of Carbonic Anhydrase (CA) Towards Alpha-Amylase (AA 1) and Glucoamylase (AMG A) Combo in One-Step Fermentation Process All treatments were evaluated via mini-scale fermentations. 410 g of ground yellow dent corn (with an average particle size around 0.5 mm) was added to 590 g tap water. This mixture was supplemented with 3.0 ml 1 g/L penicillin and 1 g of urea. The pH of this slurry was adjusted to 4.5 with 40% $H_2SO_4$. Dry solid (DS) level was determined to be 35 wt.-%. Approximately 5 g of this slurry was added to 20 ml vials. Each vial was dosed with the appropriate amount of enzyme dosage shown in Table 1 below followed by addition of 200 micro liters yeast propagate/5 g slurry (RED STAR™). Actual enzyme dosages were based on the exact weight of corn slurry in each vial. Vials were incubated at 32° C. Nine replicate fermentations of each treatment were run. Three replicates were selected for 24 hours, 48 hours and 70 hours time point analysis. Vials were vortexed at 24, 48 and 70 hours and analyzed by HPLC. The HPLC preparation consisted of stopping the reaction by addition of 50 microliters of 40% $H_2SO_4$, centrifuging, and filtering through a 0.45 micrometer filter. Samples were stored at 4° C. until analysis. Agilent™ 1100 HPLC system coupled with RI detector was used to determine ethanol and oligosaccharides concentration. The separation column was Aminex HPX-87H on exclusion column (300 mm×7.8 mm) from BioRad™.

TABLE 1

| | Treatments | AA 1 dose (FAU-F/g DS) | AMG A dose (AGU/g DS) | CA dose (Units/g DS) |
|---|---|---|---|---|
| 1 | AA 1 + AMG A | 0.0475 | 0.50 | — |
| 2 | AA 1 + AMG A + CA (X) | 0.0475 | 0.50 | 2,886 |
| 3 | AA 1 + AMG A + CA (Y) | 0.0475 | 0.50 | 11,544 |

Result

| | CA (units/g DS) | | |
|---|---|---|---|
| Time (hr) | 0 | X | Y |
| 24 hours | 105.23 | 107.13 | 108.34 |
| 48 hours | 148.70 | 151.22 | 152.66 |
| 70 hours | 159.79 | 162.65 | 163.77 |

Ethanol yield with time and carbonic anhydrase at different concentrations.

The result is also displayed in FIG. 1

The invention claimed is:

1. A process of producing a fermentation product from starch-containing material comprising the steps of:
   i) liquefying starch-containing material with an alpha-amylase;
   ii) saccharifying the liquefied material with a carbohydrate source generating enzyme,
   iii) fermenting with one or more fermenting organisms by adding a carbonic anhydrase before or during fermentation.

2. The process of claim 1, wherein the carbonic anhydrase is selected from the carbonic anhydrase classes alpha, beta, and gamma.

3. The process of claim 1, wherein the carbonic anhydrase is derived from a strain of *Bacillus, Methanobacterium*, or *Methanosarcina*.

4. The process of claim 1, wherein the carbonic anhydrase is present or added in a concentration of 100-100,000 Units/g dry solids.

5. The process of claim 1, wherein the fermenting organism is a strain of *Pichia* or *Saccharomyces*.

6. The process of claim 1, wherein the carbonic anhydrase is added to the fermentation medium when the fermenting organism is in the lag phase.

7. The process of claim 1, wherein the carbonic anhydrase is added to the fermentation medium when the fermenting organism is in exponential phase or stationary phase.

8. The process of claim 1, wherein the carbonic anhydrase is added to the fermentation medium simultaneous with or after an alpha-amylase or carbohydrate-source generating enzyme is added.

9. The process of claim 1, wherein the plant material is starch-containing material selected from the group consisting of corn, cassava, wheat, barley, rye, milo and potatoes; or any combination thereof.

10. The process of claim 1, further comprising, prior to the step i), the steps of:
    x) reducing the particle size of starch-containing material; and
    y) forming a slurry comprising the starch-containing material and water.

* * * * *